(12) United States Patent
Mahapatra et al.

(10) Patent No.: US 10,702,335 B2
(45) Date of Patent: Jul. 7, 2020

(54) ELECTRODE CATHETER FOR ABLATION PURPOSES AND RELATED METHOD THEREOF

(71) Applicant: University of Virginia Patent Foundation, Charlottesville, VA (US)

(72) Inventors: Srijoy Mahapatra, Charlottesville, VA (US); George T. Gillies, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 510 days.

(21) Appl. No.: 14/967,923

(22) Filed: Dec. 14, 2015

(65) Prior Publication Data

US 2016/0331445 A1   Nov. 17, 2016

Related U.S. Application Data

(63) Continuation of application No. 12/532,233, filed as application No. PCT/US2008/057626 on Mar. 20, 2008, now Pat. No. 9,211,405.

(Continued)

(51) Int. Cl.
*A61B 18/14* (2006.01)
*A61N 1/06* (2006.01)
(Continued)

(52) U.S. Cl.
CPC ............ *A61B 18/1492* (2013.01); *A61N 1/06* (2013.01); *A61B 2017/003* (2013.01);
(Continued)

(58) Field of Classification Search
CPC .......... A61B 18/1492; A61B 2017/003; A61B 2017/00323; A61B 2018/00029;
(Continued)

(56) References Cited

U.S. PATENT DOCUMENTS

| 3,794,026 A | 2/1974 | Jacobs |
| 3,814,104 A * | 6/1974 | Irnich ................. A61N 1/0573 |
| | | 607/128 |

(Continued)

FOREIGN PATENT DOCUMENTS

| AU | 7052296 | 1/1997 |
| CA | 2236958 | 11/1998 |

(Continued)

OTHER PUBLICATIONS

U.S. Appl. No. 12/530,938, Final Office Action dated Sep. 30, 2015, 24 pages.

(Continued)

*Primary Examiner* — Michael F Peffley
(74) *Attorney, Agent, or Firm* — Jenkins, Wilson, Taylor & Hunt, P.A.

(57) ABSTRACT

An electrode catheter for use with an endocardial ablation catheter, wherein the electrode catheter receives the transmitted energy for ablating a portion of the heart. The electrode catheter comprises a proximal portion, a distal portion, and a longitudinal structure there between; and an electrode in communication with said electrode catheter, wherein said electrode receives the transmitted energy from the endocardial ablation catheter, or alternatively an epicardial ablation catheter.

17 Claims, 8 Drawing Sheets

Related U.S. Application Data

(60) Provisional application No. 60/919,351, filed on Mar. 22, 2007.

(51) Int. Cl.
*A61B 17/00* (2006.01)
*A61B 18/00* (2006.01)
*A61B 90/00* (2016.01)

(52) U.S. Cl.
CPC ............ *A61B 2017/00323* (2013.01); *A61B 2018/00029* (2013.01); *A61B 2018/00035* (2013.01); *A61B 2018/00279* (2013.01); *A61B 2018/00357* (2013.01); *A61B 2018/00363* (2013.01); *A61B 2018/00577* (2013.01); *A61B 2018/00916* (2013.01); *A61B 2018/1497* (2013.01); *A61B 2090/064* (2016.02); *A61B 2218/002* (2013.01); *A61B 2218/007* (2013.01)

(58) Field of Classification Search
CPC ........... A61B 2018/00035; A61B 2018/00279; A61B 2018/00357; A61B 2018/00464; A61B 2018/00577; A61B 2018/00916; A61B 2018/1497
See application file for complete search history.

(56) References Cited

U.S. PATENT DOCUMENTS

| | | |
|---|---|---|
| 4,349,023 A | 9/1982 | Gross |
| 4,607,644 A | 8/1986 | Pohndorf |
| 4,817,634 A | 4/1989 | Holleman et al. |
| 4,935,008 A | 6/1990 | Lewis, Jr. |
| 4,971,070 A | 11/1990 | Holleman et al. |
| 4,991,603 A | 2/1991 | Cohen et al. |
| 5,033,477 A | 7/1991 | Chin et al. |
| 5,071,428 A | 12/1991 | Chin et al. |
| 5,158,097 A | 10/1992 | Christlieb |
| 5,213,570 A | 5/1993 | VanDeripe |
| 5,269,326 A | 12/1993 | Verrier |
| 5,300,110 A | 4/1994 | Latterell et al. |
| 5,335,313 A | 8/1994 | Douglas |
| 5,336,252 A | 8/1994 | Cohen |
| 5,395,349 A | 3/1995 | Quiachon et al. |
| 5,465,711 A | 11/1995 | Moll et al. |
| 5,484,423 A | 1/1996 | Waskonig et al. |
| 5,500,012 A * | 3/1996 | Brucker ............... A61B 5/0422 604/22 |
| 5,509,924 A | 4/1996 | Paspa et al. |
| 5,544,654 A | 8/1996 | Murphy et al. |
| 5,662,647 A | 9/1997 | Crow et al. |
| 5,669,882 A | 9/1997 | Pyles |
| 5,702,438 A | 12/1997 | Avitall |
| 5,725,504 A | 3/1998 | Collins |
| 5,733,280 A | 3/1998 | Avitall |
| 5,779,699 A | 7/1998 | Lipson |
| 5,792,217 A | 8/1998 | Camps et al. |
| 5,797,870 A | 8/1998 | March et al. |
| 5,800,428 A | 9/1998 | Nelson et al. |
| 5,807,249 A | 9/1998 | Qin et al. |
| 5,812,978 A | 9/1998 | Nolan |
| 5,827,216 A | 10/1998 | Igo et al. |
| 5,843,048 A | 12/1998 | Gross |
| 5,846,239 A | 12/1998 | Swanson et al. |
| 5,868,741 A * | 2/1999 | Chia ................. A61B 18/1492 606/41 |
| 5,885,217 A | 3/1999 | Gisselberg et al. |
| 5,916,194 A | 6/1999 | Jacobsen et al. |
| 5,928,191 A * | 7/1999 | Houser ............ A61B 18/1492 128/898 |
| 5,931,810 A | 8/1999 | Grabek |
| 5,970,457 A | 10/1999 | Brant et al. |
| 5,972,013 A | 10/1999 | Schmidt |
| 6,032,674 A | 3/2000 | Eggers et al. |
| 6,036,685 A | 3/2000 | Mueller |
| 6,051,008 A | 4/2000 | Saadat et al. |
| 6,120,476 A | 9/2000 | Fung et al. |
| 6,123,084 A | 9/2000 | Jandak et al. |
| 6,148,825 A | 11/2000 | Anderson et al. |
| 6,156,009 A | 12/2000 | Grabek |
| 6,156,018 A | 12/2000 | Hassett |
| 6,162,195 A | 12/2000 | Igo et al. |
| 6,200,303 B1 | 3/2001 | Verrior et al. |
| 6,200,315 B1 | 3/2001 | Gaiser et al. |
| 6,206,004 B1 | 3/2001 | Schmidt et al. |
| 6,206,874 B1 * | 3/2001 | Ubby ................... A61B 5/0422 600/508 |
| 6,216,704 B1 * | 4/2001 | Ingle ................. A61B 18/1482 128/898 |
| 6,231,518 B1 * | 5/2001 | Grabek ................. A61B 10/06 600/508 |
| 6,237,605 B1 | 5/2001 | Vaska et al. |
| 6,263,241 B1 | 7/2001 | Rosborough et al. |
| 6,266,567 B1 | 7/2001 | Ishikawa et al. |
| 6,270,476 B1 | 8/2001 | Santoianni et al. |
| 6,270,484 B1 | 8/2001 | Yoon |
| 6,273,877 B1 | 8/2001 | West et al. |
| 6,278,975 B1 | 8/2001 | Brant et al. |
| 6,314,963 B1 | 11/2001 | Vaska et al. |
| 6,322,536 B1 | 11/2001 | Rosengart et al. |
| 6,325,776 B1 | 12/2001 | Anderson et al. |
| 6,416,505 B1 | 7/2002 | Fleischman et al. |
| 6,423,051 B1 | 7/2002 | Kaplan et al. |
| 6,500,130 B2 | 12/2002 | Kinsella et al. |
| 6,527,767 B2 | 3/2003 | Wang et al. |
| 6,551,289 B1 | 4/2003 | Higuchi et al. |
| 6,554,809 B2 | 4/2003 | Aves |
| 6,558,382 B2 | 5/2003 | Jahns et al. |
| 6,569,082 B1 | 5/2003 | Chin |
| 6,579,288 B1 | 6/2003 | Swanson et al. |
| 6,592,552 B1 | 7/2003 | Schmidt |
| 6,602,242 B1 * | 8/2003 | Fung ................. A61B 18/1492 600/373 |
| 6,613,062 B1 | 9/2003 | Leckrone et al. |
| 6,616,676 B2 | 9/2003 | Bashiri et al. |
| 6,666,844 B1 | 12/2003 | Igo et al. |
| 6,666,861 B1 | 12/2003 | Grabek |
| 6,689,128 B2 | 2/2004 | Sliwa, Jr. et al. |
| 6,711,436 B1 | 3/2004 | Duhaylongsod |
| 6,723,092 B2 | 4/2004 | Brown et al. |
| 6,752,805 B2 | 6/2004 | Maguire et al. |
| 6,771,996 B2 | 8/2004 | Bowe et al. |
| 6,783,510 B1 | 8/2004 | Gibson et al. |
| 6,786,898 B2 | 9/2004 | Guenst |
| 6,811,544 B2 | 11/2004 | Schaer |
| 6,827,714 B2 * | 12/2004 | Swanson ............ A61B 18/1492 606/32 |
| 6,827,715 B2 | 12/2004 | Francischelli et al. |
| 6,835,193 B2 | 12/2004 | Epstein et al. |
| 6,837,848 B2 | 1/2005 | Bonner et al. |
| 6,837,886 B2 | 1/2005 | Collins et al. |
| 6,849,075 B2 | 2/2005 | Bertolero et al. |
| 6,868,291 B1 | 3/2005 | Bonner et al. |
| 6,869,414 B2 | 3/2005 | Simpson et al. |
| 6,876,885 B2 | 4/2005 | Swoyer et al. |
| 6,899,710 B2 | 5/2005 | Hooven |
| 6,916,318 B2 | 7/2005 | Francischelli et al. |
| 6,918,890 B2 | 7/2005 | Schmidt |
| 6,918,908 B2 | 7/2005 | Bonner et al. |
| 6,921,295 B2 | 7/2005 | Sommer et al. |
| 6,928,313 B2 | 8/2005 | Peterson |
| 6,936,040 B2 | 8/2005 | Kramm et al. |
| 6,960,205 B2 | 11/2005 | Jahns et al. |
| 6,968,223 B2 | 11/2005 | Hanover |
| 6,973,352 B1 | 12/2005 | Tsutsui et al. |
| 6,974,454 B2 | 12/2005 | Hooven |
| 7,004,937 B2 | 2/2006 | Lentz et al. |
| 7,008,418 B2 | 3/2006 | Hall et al. |
| 7,027,876 B2 | 4/2006 | Casavant et al. |
| 7,037,296 B2 | 5/2006 | Kadziauskas et al. |
| 7,041,099 B2 | 5/2006 | Thomas et al. |
| 7,048,733 B2 | 5/2006 | Hartley et al. |
| 7,059,878 B1 | 6/2006 | Hendrixson |

(56) References Cited

U.S. PATENT DOCUMENTS

| | | |
|---|---|---|
| 7,063,693 B2 | 6/2006 | Guenst |
| 7,085,606 B2 | 8/2006 | Flach et al. |
| 7,089,063 B2 | 8/2006 | Lesh et al. |
| 7,090,637 B2 | 8/2006 | Danitz et al. |
| 7,101,362 B2 | 9/2006 | Vanney |
| 7,104,986 B2 | 9/2006 | Hovda et al. |
| 7,120,504 B2 | 10/2006 | Osypka |
| 7,130,699 B2 | 10/2006 | Huff et al. |
| 7,142,919 B2 | 11/2006 | Hine et al. |
| 7,146,225 B2 | 12/2006 | Guenst et al. |
| 7,147,633 B2 | 12/2006 | Chee et al. |
| 7,207,988 B2 | 4/2007 | Leckrone et al. |
| 7,214,180 B2 | 5/2007 | Chin |
| 7,226,448 B2 | 6/2007 | Bertolero et al. |
| 7,226,458 B2 | 6/2007 | Kaplan et al. |
| 7,232,422 B2 | 6/2007 | Gibson et al. |
| 7,247,139 B2 | 7/2007 | Yudkovitch et al. |
| 7,259,906 B1 | 8/2007 | Islam |
| 7,264,587 B2 | 9/2007 | Chin |
| 7,286,992 B2 | 10/2007 | Sander et al. |
| 7,309,328 B2 | 12/2007 | Kaplan et al. |
| 7,398,781 B1 | 7/2008 | Chin |
| 7,468,029 B1 | 12/2008 | Robertson, Jr. |
| 8,048,072 B2 * | 11/2011 | Verin ................. A61B 5/4233 606/34 |
| 8,271,095 B2 | 9/2012 | O'Sullivan |
| 9,211,405 B2 | 12/2015 | Mahapatra et al. |
| 2001/0001314 A1 | 5/2001 | Davison et al. |
| 2001/0020166 A1 | 9/2001 | Daly et al. |
| 2001/0025178 A1 | 9/2001 | Mulier et al. |
| 2001/0039410 A1 | 11/2001 | Verrier et al. |
| 2001/0056280 A1 | 12/2001 | Underwood et al. |
| 2002/0002372 A1 | 1/2002 | Jahns et al. |
| 2002/0019626 A1 | 2/2002 | Sharkey et al. |
| 2002/0045895 A1 | 4/2002 | John, Jr. et al. |
| 2002/0055714 A1 | 5/2002 | Rothschild |
| 2002/0058925 A1 | 5/2002 | Kaplan et al. |
| 2002/0072737 A1 | 6/2002 | Belden et al. |
| 2002/0077600 A1 | 6/2002 | Sirimanne |
| 2002/0082523 A1 | 6/2002 | Kinsella et al. |
| 2002/0161361 A1 | 10/2002 | Sherman et al. |
| 2003/0028187 A1 | 2/2003 | Vaska et al. |
| 2003/0065318 A1 | 4/2003 | Pendekanti |
| 2003/0069572 A1 | 4/2003 | Wellman et al. |
| 2003/0114796 A1 | 6/2003 | Schmidt |
| 2003/0181855 A1 | 9/2003 | Simpson et al. |
| 2004/0024397 A1 | 2/2004 | Griffin, III et al. |
| 2004/0024413 A1 | 2/2004 | Lentz et al. |
| 2004/0024435 A1 | 2/2004 | Leckrone et al. |
| 2004/0034365 A1 | 2/2004 | Lentz et al. |
| 2004/0064138 A1 | 4/2004 | Grabek |
| 2004/0068312 A1 | 4/2004 | Sigg et al. |
| 2004/0087831 A1 | 5/2004 | Michels et al. |
| 2004/0087938 A1 | 5/2004 | Leckrone et al. |
| 2004/0102804 A1 | 5/2004 | Chin |
| 2004/0138526 A1 | 7/2004 | Guenst |
| 2004/0138527 A1 | 7/2004 | Bonner et al. |
| 2004/0138531 A1 | 7/2004 | Bonner et al. |
| 2004/0147826 A1 | 7/2004 | Peterson |
| 2004/0186507 A1 | 9/2004 | Hall et al. |
| 2004/0215168 A1 | 10/2004 | Verrier et al. |
| 2004/0216748 A1 | 11/2004 | Chin |
| 2004/0267303 A1 | 12/2004 | Guenst |
| 2004/0267326 A1 | 12/2004 | Ocel et al. |
| 2005/0020914 A1 | 1/2005 | Amundson et al. |
| 2005/0027243 A1 | 2/2005 | Gibson et al. |
| 2005/0085769 A1 | 4/2005 | MacMahon et al. |
| 2005/0096522 A1 | 5/2005 | Reddy et al. |
| 2005/0154376 A1 | 7/2005 | Riviere et al. |
| 2005/0234507 A1 | 10/2005 | Geske et al. |
| 2005/0251094 A1 | 11/2005 | Peterson |
| 2005/0256368 A1 | 11/2005 | Klenk et al. |
| 2005/0261673 A1 | 11/2005 | Bonner et al. |
| 2005/0273006 A1 | 12/2005 | Stewart et al. |
| 2005/0273144 A1 | 12/2005 | Lennox |
| 2006/0025705 A1 | 2/2006 | Whittaker et al. |
| 2006/0025762 A1 | 2/2006 | Mohan et al. |
| 2006/0041243 A1 | 2/2006 | Nayak et al. |
| 2006/0052660 A1 | 3/2006 | Chin |
| 2006/0064056 A1 | 3/2006 | Coyle et al. |
| 2006/0064058 A1 | 3/2006 | Coyle |
| 2006/0074397 A1 | 4/2006 | Shimada |
| 2006/0106442 A1 | 5/2006 | Richardson et al. |
| 2006/0122591 A1 | 6/2006 | Keidar |
| 2006/0189840 A1 | 8/2006 | Walsh et al. |
| 2006/0200002 A1 | 9/2006 | Guenst |
| 2006/0229490 A1 | 10/2006 | Chin |
| 2006/0247522 A1 | 11/2006 | McGee |
| 2006/0247672 A1 | 11/2006 | Vidlund et al. |
| 2006/0259017 A1 | 11/2006 | Heil, Jr. et al. |
| 2006/0270900 A1 | 11/2006 | Chin et al. |
| 2006/0271032 A1 | 11/2006 | Chin et al. |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0032796 A1 | 2/2007 | Chin-Chen et al. |
| 2007/0038052 A1 | 2/2007 | Swoyer et al. |
| 2007/0043397 A1 | 2/2007 | Ocel et al. |
| 2007/0055142 A1 | 3/2007 | Webler |
| 2007/0198041 A1 | 8/2007 | Rupp et al. |
| 2007/0270882 A1 | 11/2007 | Hjelle et al. |
| 2008/0015625 A1 | 1/2008 | Ventura et al. |
| 2008/0051671 A1 | 2/2008 | Broome et al. |
| 2008/0091109 A1 | 4/2008 | Abraham |
| 2008/0097399 A1 | 4/2008 | Sachar et al. |
| 2008/0108945 A1 | 5/2008 | Kaplan et al. |
| 2008/0183080 A1 | 7/2008 | Abraham |
| 2008/0208184 A1 | 8/2008 | Davies |
| 2008/0262432 A1 | 10/2008 | Miller |
| 2008/0294174 A1 | 11/2008 | Bardsley et al. |
| 2009/0030469 A1 | 1/2009 | Meiry |
| 2010/0069849 A1 | 3/2010 | Kassab |
| 2010/0094143 A1 | 4/2010 | Mahapatra et al. |
| 2010/0114093 A1 | 5/2010 | Mahapatra et al. |
| 2010/0211064 A1 | 8/2010 | Mahapatra et al. |
| 2010/0241185 A1 | 9/2010 | Mahapatra et al. |

FOREIGN PATENT DOCUMENTS

| | | |
|---|---|---|
| DE | 4313903 C1 | 9/1994 |
| EP | 0134367 A1 | 3/1985 |
| EP | 0450608 A1 | 10/1991 |
| EP | 1129681 A1 | 9/2001 |
| EP | 1181896 A1 | 2/2002 |
| EP | 2279773 | 2/2011 |
| WO | 8704081 | 7/1987 |
| WO | 9320878 | 10/1993 |
| WO | 9320886 | 10/1993 |
| WO | 9510319 | 4/1995 |
| WO | 9515115 | 6/1995 |
| WO | 9733526 | 9/1997 |
| WO | WO 98/00060 A1 | 1/1998 |
| WO | 9918869 | 4/1999 |
| WO | 0105306 | 1/2001 |
| WO | 0158373 | 8/2001 |
| WO | 0168173 | 9/2001 |
| WO | 0180724 | 11/2001 |
| WO | 0180757 | 11/2001 |
| WO | WO 03/092792 A2 | 11/2003 |
| WO | 2008112870 | 9/2008 |
| WO | 2008115745 | 9/2008 |
| WO | 2008118737 | 10/2008 |
| WO | 2009062061 | 5/2009 |

OTHER PUBLICATIONS

U.S. Appl. No. 12/530,938, Final Office Action dated Nov. 21, 2013, 30 pages.
U.S. Appl. No. 12/530,938, Non-Final Office Action dated Dec. 4, 2014, 21 pages.
U.S. Appl. No. 12/530,938, Non-Final Office Action dated Jun. 25, 2012, 48 pages.

(56) References Cited

OTHER PUBLICATIONS

U.S. Appl. No. 12/530,938, Non-Final Office Action dated Feb. 26, 2013, 32 pages.
U.S. Appl. No. 12/532,233, Final Office Action dated May 15, 2013, 22 pages.
U.S. Appl. No. 12/532,233, Non-Final Office Action dated Aug. 7, 2014, 14 pages.
U.S. Appl. No. 12/532,233, Notice of Allowance dated Aug. 14, 2015, 5 pages.
U.S. Appl. No. 12/532,233, Notice of Allowance dated Apr. 2, 2015, 7 pages.
U.S. Appl. No. 12/532,233, Non-Final Office Action dated Oct. 26, 2012, 18 pages.
U.S. Appl. No. 12/532,233, Non-Final Office Action dated Mar. 7, 2012, 53 pages.
U.S. Appl. No. 12/741,710, Final Office Action dated Jun. 15, 2015, 16 pages.
U.S. Appl. No. 12/741,710, Final Office Action dated Apr. 22, 2014, 24 pages.
U.S. Appl. No. 12/741,710, Non-Final Office Action dated Jul. 3, 2013, 14 pages.
U.S. Appl. No. 12/741,710, Office Action dated Nov. 8, 2012, 54 pages.
European Patent Application No. 10846297.9, Office Action dated Jul. 1, 2014, 5 pages.
Arrow International Corporation, AN-05505 Epidural Needle, Available online at vvww.arrowintl.com/products/boms/AN05505.asp?cat=17&item=AN-05505&xsec=.
Beukema, Radiofrequency Ablation of Atrial Fibrillation in Patients Undergoing Concommitant Cardiac Surgery. First Experience, Pace, vol. 20, Part 2, 1997, pp. 1100.
D'Avila, "Transthoracic Epicardial Catheter Ablation of Ventricular Tachycardia," Heart Rhythmn, 2006, p. 1110-1111, vol. 3.
Derose, Robotically Assisted Left Ventricular Epicardial Lead Implantation for Biventricular Pacing: the Posterior Approach, The Annals of Thoracic Surgery, vol. 77, 2004, pp. 1472-1474.
Frolich, Pioneers in Epidural Needle Design, Anesthesia & Analgesia, vol. 93, 2001, pp. 215-220.
Hansky, Lead Selection and Implantation Technique for Biventricular Pacing, European Heart Journal Supplements, vol. 6, Supplement D, 2004, pp. D112-D116.
Klein, Radiofrequency Ablation of Cardiac Arrhythmias, Scientific American Science & Medicine, 1994, pp. 48-57.
Lin, Catheter Microwave Ablation Therapy for Cardiac Arrhythmias, Bioelectromagnetics, vol. 20, 1999, pp. 120-132.
Mahapatra, Access Device and Manometric Monitoring System for Epicardial Electrophysiology: Improved Porototype and Use in Human Trials, Technical Report No. UVA/640419/MAE08/102, Jan. 2008.
Mahapatra, Access Device and Manometric Monitoring System for Epicardial Electrophysiology: Improved Porototype and Use in Human Trials, Technical Report No. UVA/640419/MAE08/101, Jul. 2007.
Mahapatra, Incidence and Predictors of Cardiac Perforation after Permanent Pacemaker Placement, Heart Rhythm, vol. 2, No. 9, 2005, pp. 907-911.
Mair, Epicardial Lead Implantation Techniques for Biventricular Pacing via Left Lateral Mini-Thoracotomy, Video-Assisted Thoracoscopy, and Robotic Approach, the Heart Surgery Forum #2003-4883, vol. 6, No. 5, 2003, pp. 412-417.
Moses, Sirolimus-Eluting Stents Versus Standard Stents in Patients with Stenosis in a Native Coronary Artery, New England Journal of Medicine, vol. 349, No. 14, 2003, pp. 1315-1323.
Omega Engineering Inc., DP25B-S Strain Gage Pagel Meter: User's Guide, Stamford, CT. Online available at http://vvww.omega.com/Manuals/manualpdf/M3598.pdf, 2002, 68 pages.
Omega Engineering Inc., DPI 603 Portable Pressure Calibrator User Guide, Stamford, CT. Available online at http://www.omega.com/Manuals/manual.pdf/M2913.pdf, 1996, 41 pages.
Omega Engineering Inc., PX26 Series Pressure Transducers: Instruction Sheet, Stamford, CT. Available online at http://vvww.omega.com/Manuals/manualpdf/M1608.pdf, 2004, 2 pages.
Omega Engineering, Inc., DP41B Universal Input Meter: User's Guide, Stamford, CT. Available online at http://www.omega.com/Manuals/manualpdf.M2544.pdf, 2005, 132 pages.
Omega Engineering, Inc., PX26 Series Pressure Transducers: Instruction Sheet, Stamford, CT. Available online at http//www.omega.com/Pressure/pdf/PX26.pdf, 2004, 1 page.
Packer, Multimodality 3-D Ultrasound and Computed Tomographic Image Fusion: A Novel Basis for Catheter Navigation and Electroanatomic Mapping, Circulation, Clinical Science, vol. 112, No. 17, Supplement 11, #2939, 2005.
Sarabanda, Efficacy and Safety of Circumferential Pulmonary Vein Isolation Using a Novel Cryothermal Balloon Ablation System, Journal of the American College of Cardiology, vol. 46, No. 10, 2005, pp. 1902-1912.
Sosa, Epicardial Mapping and Ablation Techniques to Control Ventricular Tachycardia, Journal of Cardiovascular Electrophysiology, vol. 16, No. 4, 2005, pp. 449-452.
Sosa, Nonsurgical Transthoracic Epicardial Approach in Patients with Ventricular Tachycardia and Previous Cardiac Surgery, Journal of Interventional Cardiac Electrophysiology, vol. 10, 2004, pp. 281-288.
Sosa, Percutaneous Pericardia! Access for Mapping and Ablation of Epicardial Ventricular Tachycardias, Circulation, Journal of the American Heart Association, vol. 115, 2007, pp. e542-e544.
Sosa, Transthoracic Epicardial Catheter Ablation of Ventricular Tachycardia, Heart Rhythm, vol. 3, 2006, pp. 1110-1111.
Stokes, U.S. Statutory Invention Registration H356, Nov. 3, 1987.
Thomas, Analysis of Human Epidural Pressures, Regional Anesthesia, vol. 17, No. 4, 1992, pp. 212-215.
Tomaske, Do Daily Threshold Trend Fluctuations of Epicardial Leads Correlate with Pacing and Sensing Characteristics in Paediatric Patients, Europace, vol. 9, 2007, pp. 662-668.
Aupperle et al., "Ablation of Atrial Fibrillation and Esophageal Injury: Effects of Energy Source and Ablation Technique," Journal of Thoracic and Cardiovascular Surgery, vol. 130, No. 6, pp. 1549-1554, (2005).
IPRP with Written Opinion and International Search Report corresponding to International Patent Application No. PCT/US2008/057626 dated Sep. 22, 2009.
Scanavacca et al., "Catheter Ablation of Atrial Fibrillation. Techniques and Results," Arquivos Brasileiros de Cardiologia, vol. 85, No. 4, 7 pps., (2005).
Tungjitkusolmun et al., "Finite Element Analyses of Uniform Curren Density Electrodes for Raio-Frequency Cardiac Ablation," IEEE Transactions on Biomedical Engineering, vol. 47, No. 1, pp. 32-40, (2000).
Müller et al., "Application of CVD-diamond for catheter ablation in the heart," Diamond and Related Materials, vol. 13, pp. 1080-1083 (2004).
Petersen et al., "Mechanisms for Enlarging Lesion Size During Irrigated Tip Radiofrequency Ablation: Is There a Virtual Electrode Effect?" Journal of Interventional Cardiology, vol. 17, No. 3, pp. 171-177 (2004).
Schwartzman et al., "Catheter Ablation of Ventricular Tachycardia Associated with Remote Myocardial Infaction: Utility of the Atrial Transseptal Approach," Journal of Interventional Cardiac Electrophysiology, vol. 1, pp. 67-71 (1997).

\* cited by examiner

ELECTRODE CATHETER FOR ABLATION PURPOSES AND RELATED METHOD THEREOF

CROSS-REFERENCES TO RELATED APPLICATIONS

The present invention is a continuation application of U.S. Pat. No. 9,211,405, issued Dec. 15, 2015, which is a 371 application of PCT/US2008/057626, which claims priority to U.S. Provisional Application Ser. No. 60/919,351 filed Mar. 22, 2007, entitled "Epicardial-Cathode Catheter for Ablation Purposes and Related Method Thereof," the disclosures of all of which are hereby incorporated by reference herein in their entireties.

This application is related to PCT International Application No. Serial No. PCT/US2008/056643, filed Mar. 12, 2008, entitled, "Access Needle Pressure Sensor Device and Method of Use," which claims benefit of priority from U.S. Provisional Application Ser. No. 60/918,782, filed Mar. 19, 2007, entitled "Manometrically Monitored Introducer Needle and Method of Use;" the disclosures of which are hereby incorporated by reference herein in their entireties.

This application is related to PCT International Application No. Ser. No. PCT/US2008/056816, filed Mar. 13, 2008, entitled, "Epicardial Ablation Catheter and Method of Use," which claims benefit of priority from U.S. Provisional Application Ser. No. 60/906,689, filed Mar. 13, 2007, entitled "Epicardial Ablation Catheter and Access Sheath and Method of Use;" the disclosures of which are hereby incorporated by reference herein in their entireties.

TECHNICAL FIELD

The present invention relates generally to the field of medical devices to be used for cardiological procedures. More specifically, the invention is in the subfield of catheterization devices and other tools to be used for cardiac ablation and in electrophysiological procedures.

BACKGROUND OF THE INVENTION

Cardiac arrhythmias are a widespread medical condition facing physicians today. Their most frequent cause is an abnormal routing of electricity though the cardiac tissue. While several surgical approaches have been developed for the purpose of treating or preventing different types of cardiac arrhythmias, ablation is now widely used as the preferred treatment. Typically, a physician places an endocardial catheter with an electrode at its tip inside the heart at a location where cells are giving off abnormal electrical signals. The electrode is activated according to various known modes of operation such that the adjacent targeted tissue is ablated and rendered non-conductive, halting the spread of improper cardiac signals.

The arrhythmia substrate is often deep in the wall of the heart, or transmural. Thus, the clinician performing the ablation wants the input energy and resulting heat to propagate entirely through the endocardium to the epicardium, thus thoroughly lesioning the substrate in question. However, critical structures lie directly outside the epicardium, and the fundamental conflict is one of depositing energy deep within the heart tissue on the one hand, but not damaging tissues, organs and structures beyond the heart wall, on the other. As an example, on average the esophagus in only 2 mm from the atrial epicardium yet the atrial is 3 mm thick. Therefore, ablationists essentially want to burn deep enough, but not too deep.

Although simple ablations are performed with relatively few complications, some of the more complex ablations that have been developed recently use more energy over longer periods of time. For example, whereas the standard ablation for atrioventricular nodal reentry requires only 60 seconds of burning, a standard ablation for atrial fibrillation (AF) may require 4000 seconds of burning. Furthermore, whereas traditional ablations are often done on the inner walls of the heart, the more complex ablations are often performed on the heart's free wall, which is even closer to the lungs, phrenic nerve, and esophagus. Recent case reports have shown complications and even death from burns that damage these structures after an AF ablation.

Modern radio frequency ablation catheter procedures operate by delivering current between a small (2-8 mm) anode located in the tip of a standard ablation catheter coupled to a large surface area conductive cathode provided on the patient's back. Current flowing between the anode and the cathode is at its highest density at the tissue location directly adjacent to the treatment electrode. Thus, a planar sheet of the current flow can be modeled as a triangle with its apex at the ablation tip (anode) and its base on the patient's back (cathode). Though most of the burning is close to the apex of the triangle, the esophagus, lungs, and phrenic nerve are within the current density triangle. The current does not drop off sufficiently between the epicardium and the adjacent structures due to the inherent proximity.

There is therefore a need in the art for an effective electrode catheter that could be electrically coupled to an endocardial or other type of ablation catheter to provide better and safer modes of treatment. Particular needs remain for such a device with appropriate length, diameter, stabilization, steering capacity, and irrigation to allow effective energy transfers transmurally through the endocardial wall.

To overcome these limitations, we have conceived the subject device and method of use, as described in the Summary of the Invention and Detailed Description of the Drawings below.

BRIEF SUMMARY OF THE INVENTION

Because ablation lesions must be created such that electrical conductivity is halted in the localized region, it is desirable to have a cathode as close to the anode as possible. The use of two standard endocardial catheters to carry out a procedure wherein one of them served as an epicardial cathode would cause several limiting considerations that would arise from such a practice. Most generally, an endocardial catheter is simply not designed for the mechanics of epicardial use. In particular, special issues regarding device length, diameter, stabilization, and steering capabilities have to be taken into account. Furthermore, the use of two standard endocardial catheters would mean that the anode and cathode would have the same size. Generally, the cathode should present a larger surface area towards the endocardial anode so that there is more current density near the anode. Lastly, the standard endocardial catheter is not able to provide a flow of irrigation fluid that could be used to cool the electrode or to separate the epicardial surface from critical neighboring anatomical structures.

The following U.S. patent documents discuss epicardial electrodes in the context of pacing: U.S. Pat. Nos. 7,085, 606; 6,266,567; 5,509,924; 5,300,110; 4,971,070; 4,817, 634; and 4,607,644; as well as U.S. Statutory Invention Registration H356, all of which are incorporated by reference herein in their entirety. No references disclose epicardial electrodes in the context of ablation or eletrophysiological procedures.

One aspect of the present invention provides an electrode catheter disposed in the middle mediastinum of the thorax of a subject for use in ablation procedures with an endocardial ablation catheter. The electrode catheter may comprise a proximal portion, a distal portion, and a longitudinal structure there between. In accordance with the invention, the electrode catheter may further include an electrode adapted for receiving energy from the endocardial ablation catheter.

Another aspect of the present invention provides an electrode catheter disposed in the intra-cardiac space of a subject for use in ablation procedures with an epicardial ablation catheter. The electrode catheter may comprise a proximal portion, a distal portion, and a longitudinal structure there between. In accordance with the invention, the electrode catheter may further include an electrode adapted for receiving energy from the epicardial ablation catheter.

Yet another aspect of the present invention relates to a method of ablating a portion of the heart by disposing an electrode in the middle mediastinum of the thorax of a subject and receiving transmitted energy from an endocardial ablation catheter.

Further yet, another aspect of the present invention relates to a method of ablating a portion of the heart by disposing an electrode in the intra-cardiac space of a subject and receiving transmitted energy from an epicardial ablation catheter.

It should be appreciated that the present invention cardiac catheter may be place or disposed in, adjacent or proximal to any space, structure, blood vessel, vasculature or organ.

An aspect of an embodiment of the present invention comprises a method for use with an endocardial ablation catheter, which transmits energy for ablating a portion of a heart. The method may comprise: disposing an electrode in the middle mediastinum of the thorax of a subject; and receiving the transmitted energy from the endocardial ablation catheter. The middle mediastinum may include, for example, an area outside the pericardium, an area inside the pericardium, or the pericardium space itself.

An aspect of an embodiment of the present invention comprises a method for use with an epicardial ablation catheter, which transmits energy for ablating a portion of a heart. The method may comprise: disposing an electrode in the intra-cardiac space of a subject; and receiving the transmitted energy from the epicardial ablation catheter.

Advantageously, upon activation of the electrode catheter and endocardial or other type of ablation catheter, energy from the ablation catheter is transmitted through the heart wall and is received by the electrode catheter. In this way, a triangular-shaped current density pattern is formed between the endocardial or other type of ablation catheter and the electrode of the electrode catheter. Tissue within this current flow is ablated, while proximal organs are left undamaged by the ablation energy. In older methods a large electrode is placed on or in contact with the patient's back, allowing ablation energy to reach not only the heart-wall tissue, but to travel through other proximal vital organs.

The invention itself, together with further objects and attendant advantages, will best be understood by reference to the following detailed description taken in conjunction with the accompanying drawings.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention.

Figure 1:
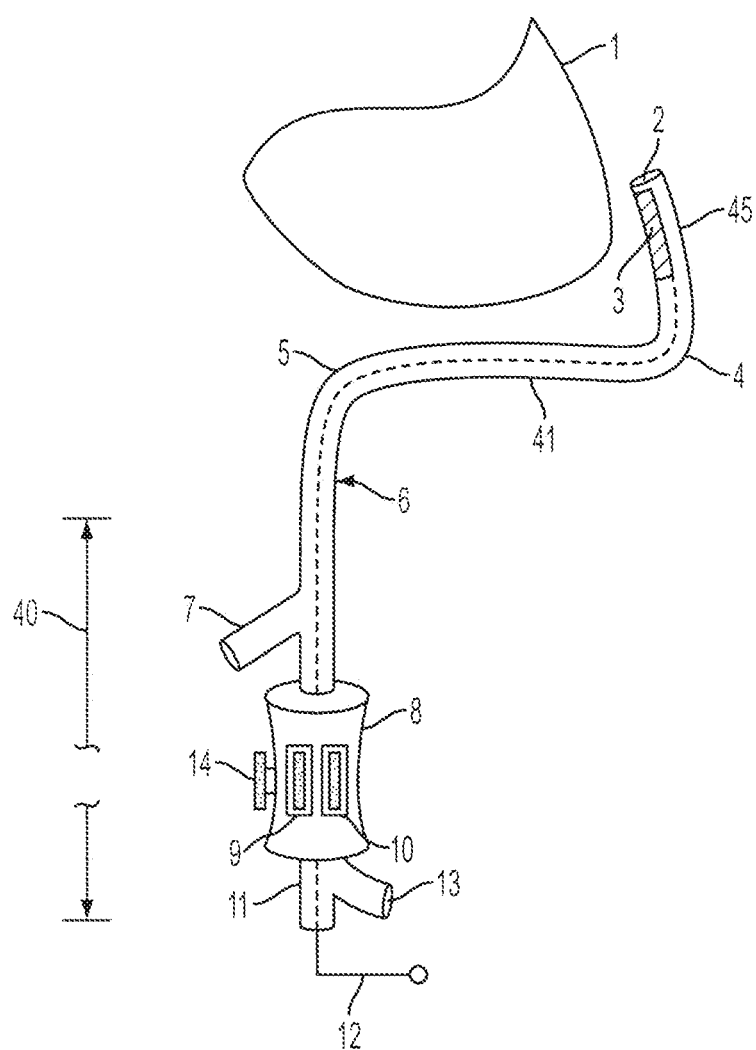
FIG. 1 schematically illustrates the overall configuration of the electrode catheter device in position relative to the heart of a patient or subject.

FIG. 1 is a schematic illustration of an overview of an exemplary embodiment of the electrode catheter 6 and its major components relative to the heart 1 of a patient being treated for a cardiac arrhythmia. The electrode catheter 6 in accordance with the present invention may comprise a proximal portion 40, a distal portion 45, and a longitudinal structure there between. It should be appreciated that the distal portion may be considered at the end tip of the catheter; or a portion or segment at or in the vicinity of the end tip of the catheter or a portion or segment leading up to (or partially up to but not all the way up to) the end tip of the catheter as desired or required. It should also be appreciated that the proximal end may be considered the tip of the beginning of the catheter; or a portion or segment at or in the vicinity of the beginning of the tip of the catheter or a portion or segment leading up to (or partially up to but not all the way up to) the beginning of the catheter, as desired or required. The distal portion 45, proximal portion 40, and longitudinal structure 45 there between may be integrally formed from a biocompatible material having requisite strength and flexibility for deployment within a patient. The electrode catheter 6 further comprises an electrode 3, which is commonly referred to in the art as a cathode. The electrode 3 is in communication with the distal portion of the catheter. The electrode 3 may be constructed of platinum, gold, sliver, iridium, or any other conducting material, alloy or other metal known in the art and is contoured for receiving energy from the endocardial ablation catheter. The electrode 3 is contoured to be compatible with proximate anatomical structures and may be semi-cylindrical in shape with a longitudinal length of between about 20 mm and about 50 mm along the catheter.

The proximal portion 40 of the catheter 6 may be implemented as desired or required along any point or segment, for example, as illustrated by the bracket in FIG. 1. It should be appreciated that the proximal portion may include, for example: a point at the proximal tip of the cathode; a portion or segment at or in the vicinity of the proximal tip of the cathode; or a portion or segment leading up to (or partially up to but not all the way up to) the proximal tip of the cathode. The length and location may vary as desired or required in order to practice the invention according to medical procedures and anatomical considerations. In summary, the proximal end may be translated in the proximal or distal direction on a case by case basis.

Figure 6:
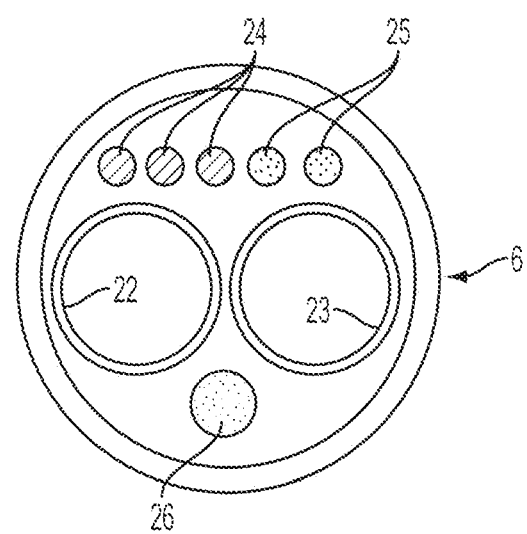
FIG. 6 schematically illustrates a cross-sectional view of the components inside the lumen of the electrode catheter.

The electrode catheter 6 may further comprises a distal fluid aperture, 2, located at the distal portion 45, a proximal fluid aperture 7 located at the proximal portion 40, and a fluid lumen 22, 23 (as shown in FIG. 6) extending longitudinally through the catheter connecting the apertures. Both the distal fluid aperture 2 and proximal fluid aperture 7 are adapted for the emitting and extracting of fluid or other medium. The fluid or other medium may be used to distend adjacent tissue and to cool the electrode during ablation procedures. The proximal fluid aperture 7 is connected to an external fluid source (not shown).

The catheter 6 further comprises a distal steering means 4 and a proximal steering means 5 which have the steering characteristics taught by Mahapatra et al. in PCT International Application No. Serial No. PCT/US2008/056816, filed Mar. 13, 2008, entitled, "Epicardial Ablation Catheter and Method of Use," hereby incorporated by reference herein in its entirety. The steering means may be guide wires, tensioning lines, pull strings, digitating distal tips, magnetic guidance means, wires, rods, chains, bands, chords, ropes, string tubes, filaments, threads, fibers, stands, other extended elements, or any other method known in the art. At the proximal end of the catheter may be a control handle 8, which may have integral to it the distal steering control means 9, the proximal steering control means 10, and the control means for the stabilization means 14. The handle is preferably sized to be grasped, held and operated by a user. It should be appreciated that other control and operating interface members, devices or means may be utilized for the handle. Attached to the proximal end of the control handle is the handle proximal port 11, which has a second fluid aperture 13, and from which the electrical lead 12 for the electrode 3 extends, in order to make electrical connections. Wire(s) (shown in FIG. 6, for example) may extend through the proximal portion to the distal portion 45 of the catheter.

Figure 4A:
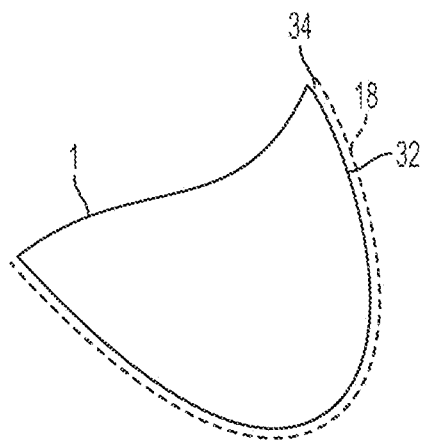
FIGS. 4(A)-(B) schematically illustrate the pericardium and heart alone (FIG. 4(A)) and the pericardium and distension thereof following an influx of fluid from the distal aperture of the electrode catheter (FIG. 4(B)).
Figure 4B:
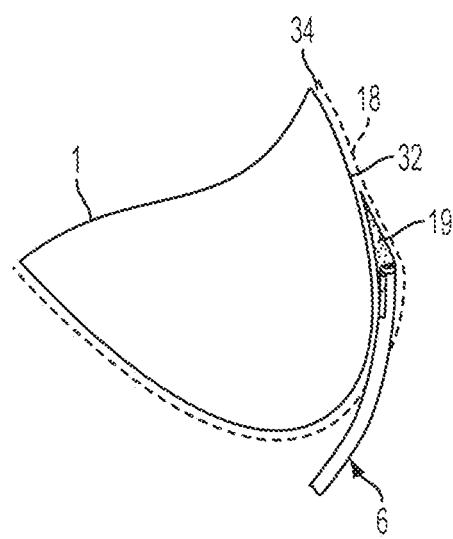

For instance, referring to FIGS. 4(A)-(C) PCT International Application No. Serial No. PCT/US2008/056816, there is provided the mechanism of action for obtaining bi-directional steering of the distal tip or portion that may be implemented for the present invention via tensioning or steering means whereby the tip or end is straight, towards the left, and towards the right, respectively.

Moreover, for instance and referring to FIGS. 4(A)-(C) PCT International Application No. Serial No. PCT/US2008/ 056816, there is provided FIGS. 7(A)-(B) are schematic illustrations of the details of an exemplary mechanism of action for directional steering of the medial segment of the device that may be implemented for the present invention.

It should be appreciated that the medium to flow through ablation catheter device or system may be at least one of the following: agent, substance, material, saline solutions, thrombolytic agents, clot lysis agents, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic agent and/or diagnostic agent, or any combination thereof.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware.

Moreover, it should be appreciated that any of the components or modules referred to with regards to any of the present invention embodiments discussed herein, may be a variety of materials and/or composites as necessary or required. Still further, it should be appreciated that any of the components or modules (or combination thereof) may provide shape, size and volume contoured by adjusting its geometry and flexibility/rigidity according to the target location or anatomy (or region, including structure and morphology of any location) being treated.

Further, it should be appreciated that the present invention ablation system may be inserted into a subject via an interventional procedure or a surgical procedure, as well as a combination thereof.

Figure 2C:
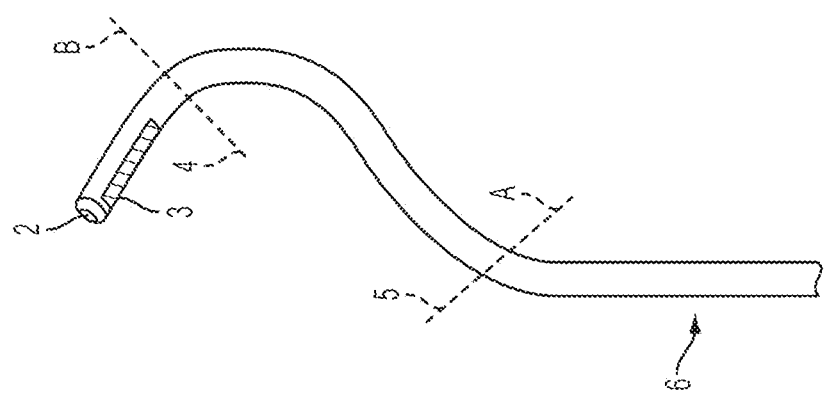
FIGS. 2(A)-(C) schematically illustrate the steering means employed to position the electrode catheter for use in ablation procedures in un-tensioned, partial steering, and full steering modes, respectively.
Figure 2B:
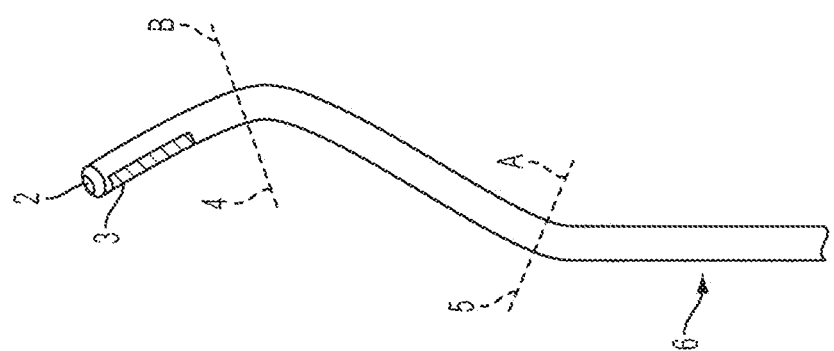
Figure 2A:
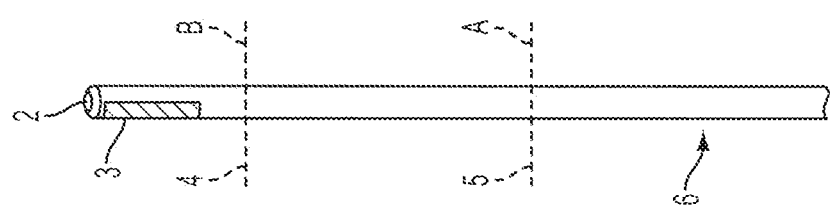

FIGS. 2(A)-(B) provide a schematic illustration of some details of an exemplary embodiment of the electrode catheter steering means in un-tensioned, partial steering, and full steering modes, respectively. The steering means are preferably of a type known in the art, including, but not limited to, guide wires, tensioning lines, pull strings, digitating distal tips, guidance means, propulsion means, or tensioning means that may be applied to the various sheaths, catheters and guidewires, or any related components disclosed herein. Steering adjustments are made along the centers of curvature, referenced as A and B, at the proximal steering means 5, and the distal 4 steering means, respectively. Specifically, FIG. 2(A) shows the electrode catheter 6 in the undeflected state. FIG. 2(B) shows the electrode catheter 6 in the partially deflected state. FIG. 2(C) shows the electrode catheter 6 in the fully deflected state as would be the case when it has been navigated into the pericardial space of a subject's heart, or other space or structure. The steering means are used to direct the electrode catheter through or navigate it within a patient's body.

It should be appreciated that the various sheaths, catheters and guidewires, or any related components disclosed herein, may have a circular or oval shaped cross-section or various combinations thereof. Further, it should be appreciated that various sheaths, catheters and guidewires, or any related components disclosed herein may have any variety of cross sections as desired or required for the medical procedure or anatomy.

Figure 3A:
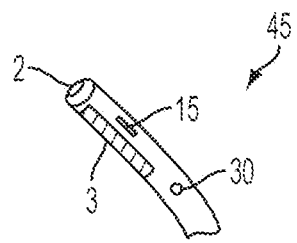
FIGS. 3(A)-(C) schematically illustrate the configuration of the distal portion of the electrode catheter in the pre-deployment and alternative deployment modes, respectively.
Figure 3B:
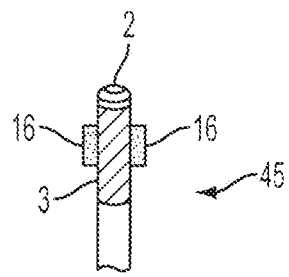
Figure 3C:
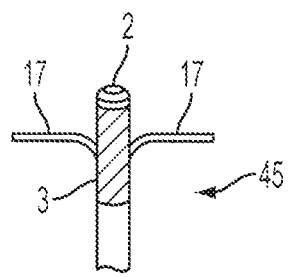

FIGS. 3(A)-(C) schematically illustrate exemplary embodiments of construction of the distal portion 45 of the electrode catheter 6. FIG. 3(A) shows a view in profile of the catheter 6 in the undeployed stage having a distal fluid aperture 2, the electrode 3, one of the two slots 15, from which a stabilization means (see FIGS. 3(B)-(C), for example) can issue or deploy, and a second fluid aperture 30. A fluid lumen and second fluid lumen (as shown in FIG. 6) may extend from the control handle 8 through the proximal portion 40 of the catheter 6 and terminate in a distal fluid aperture 2, and second distal fluid aperture 30, respectively. The fluid aperture 2 and second fluid aperture 40 are adapted for allowing the emitting and extracting of fluid or other medium as desired or required.

FIG. 3(B) schematically illustrates an example embodiment of the distal portion 45 configuration of the catheter 6 in the deployed stage for the case where the stabilization means comprises a pair of tabs 16 that have been extended from the slots 15. The stabilization means may be made of a number of non-conducting materials known in the art in order to allow the rotational orientation of the catheter to remain fixed in place relative to the surface of the heart. The stabilization tabs 16 can engage proximal anatomical structures in order to keep the electrode facing the energy source. If the catheter 6 were allowed to rotate so that the electrode faced away from the energy source, the adjacent anatomical structures could suffer burns from energy during ablation.

FIG. 3(C) schematically illustrates another example embodiment of the catheter 6 in the deployed stage in which the stabilization means is now a pair of wires 17 extending from the slots 15. In the case of either the tabs 16 or the wires 17, the control means 14 on the control handle 8 is used to regulate the degree of extension of said stabilization means via a pull-wire arrangement or some other suitable tensioning, positional adjustment or digitation means know in the art. The tabs 16 and wires 17 are just two examples of stabilization means. There are many other embodiments of stabilization means known in the art.

FIGS. 4(A) and 4(B) schematically illustrates the heart 1 and pericardium 18 of a patient. The pericardium is in close proximity to the epicardium 32. FIG. 4(B) shows an embodiment wherein the catheter 6 has had its distal portion 45 positioned in the pericardial space, cavity or sack 34, or the area between the pericardium 18 and epicardium 32. A fluid can be pumped through the distal fluid aperture 2 or second distal fluid aperture 30 (as shown in FIG. 3) in order to create a distention 19 of the pericardium. As a result, any anatomical structures, such as the esophagus and lungs that might have been as close as about 2 mm from the epicardium will now be substantially farther from it. The danger of suffering burns during ablation is, therefore, reduced or eliminated. Danger to the esophagus from ablation is described in detail by H. Aupperle et al. in their article "Ablation of Atrial Fibrillation and Esophageal Injury: Effects of Energy Source and Ablation Technique," Journal of Thoracic and Cardiovascular Surgery, Vol. 130, pp. 1549-1554, (2005), of which is hereby incorporated by reference herein. The fluid not only distends the pericardium, but also serves to cool the electrode, 3, during the ablation process.

Figure 5A:
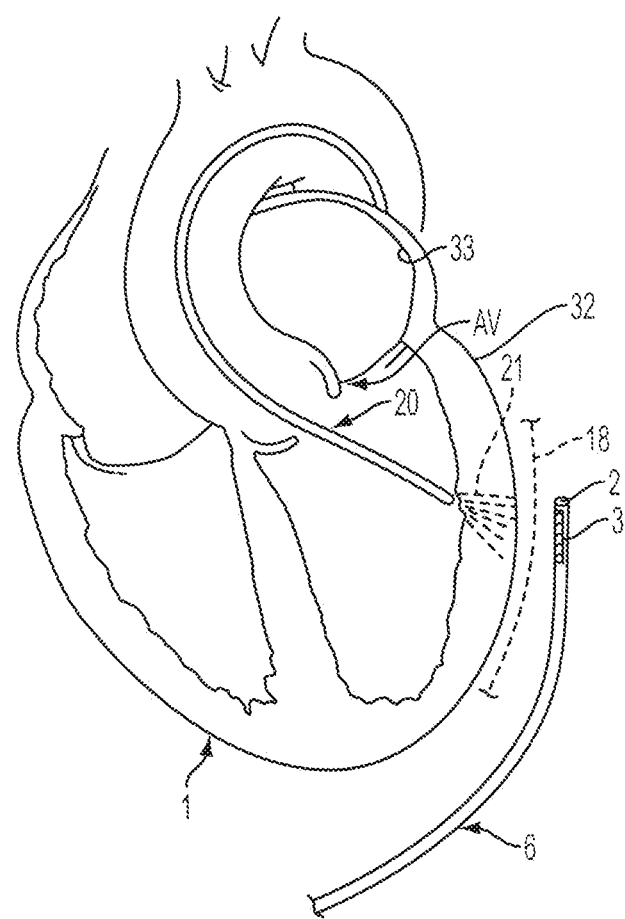
FIG. 5(A) schematically illustrates the relative positions of the endocardial ablation catheter and the electrode catheter during an ablation procedure, wherein the electrode catheter has been navigated into position outside the epicardium and pericardium.

FIG. 5(A) schematically illustrates an exemplary embodiment wherein an endocardial ablation catheter 20 is in place inside the heart 1 just inside the endocardium 33, as illustrated by D. Schwartzman et al. in FIG. 3 of their article, "Catheter Ablation of Ventricular Tachycardia Associated with Remote Myocardial Infarction: Utility of the Atrial Transseptal Approach," Journal of Interventional Cardiac Electrophysiology, Vol. 1, pp. 67-71, (1997), of which is hereby incorporated by reference herein in its entirety. The electrode catheter 6 has been navigated into position outside and in close proximity to the epicardium 32 and pericardium 18, or as desired or required. The electrode catheter 6 is oriented such that the electrode 3 faces the heart. The distal portion of the electrode catheter 45 is held in place by the stabilization means of the invention, and the ablation process is started. The electrode 3 of the electrode catheter 6 receives the current from the endocardial ablation catheter 20. In one embodiment, the ablation energy is in the form of RF waves. The characteristic triangular-shaped current density pattern 21 is then observed between the tip of the endocardial ablation catheter 20 and the electrode 3 as the majority of current density remains between the two catheters. In this way, the anatomical structures located outside the triangular-shaped current density pattern 21 are protected from burns.

Figure 5B:
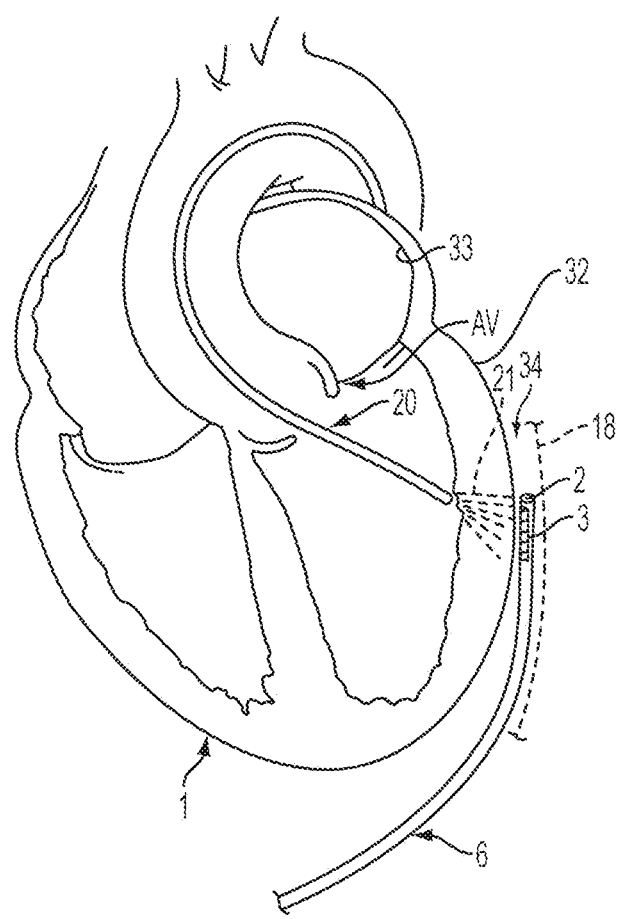
FIG. 5(B) schematically illustrates the relative positions of the endocardial ablation catheter and the electrode catheter during an ablation procedure, wherein electrode catheter has been navigated into position inside the pericardium, but outside the epicardium.

FIG. 5(B) schematically illustrates another exemplary embodiment similar to FIG. 5(A), but wherein the electrode catheter 6 is positioned between the epicardium 32 and pericardium 18 in the pericardial space, cavity or sack 34.

For instance, but not limited thereto, the electrode catheter may be disposed in the middle mediastinum, any area outside the pericardium, or any area inside the pericardium.

Although not illustrated, an embodiment of the present invention provides an endocardial electrode catheter disposed in the intra-cardiac space of a subject for use in ablation procedures with an epicardial ablation catheter. In accordance with the invention, the electrode catheter further includes an electrode adapted for receiving energy from the epicardial ablation catheter. For example, but not limited thereto, the intra-cardiac space includes the left ventricle and/or right ventricle, as well as any interior region or region in proximity to the interior of the heart.

Although not illustrated, an embodiment of the present invention provides an electrode catheter disposed in the intra-cardiac space of a subject for use in ablation procedures with an endocardial ablation catheter. In accordance with the invention, the electrode catheter further includes an electrode adapted for receiving energy from the endocardial ablation catheter. For example, but not limited thereto, the endocardial cathode catheter may be disposed in the intra-cardiac space and the endocardial ablation catheter may be in a second intra-cardiac space. The intra-cardiac spaces may be various ventricles or chambers of the heart, or any desirable or required regions of the heart.

An aspect of an embodiment of the present invention ablation system may be implemented with an access needle (introducer needle), conduit or the like. The access needle or conduit is adapted to be inserted into the epicardial region or other body part or body space so as to provide an access or guideway for the present invention ablation catheter, sheath, guidewire, etc. An example of an access system is disclosed in PCT International Application No. Serial No. PCT/US2008/056643, filed Mar. 12, 2008, entitled, "Access Needle Pressure Sensor Device and Method of Use," of which is hereby incorporated by reference herein in its entirety. See for example, but not limited thereto, FIGS. 2 and 5 of the PCT International Application No. Serial No. PCT/US2008/056643. The access needle sensor device or the like serves as a guideway for introducing other devices into the pericardium, for instance sheath catheters that might subsequently be employed for procedures in the pericardium and the epicardium of the heart, or other applicable regions, space or anatomy. Other devices that the access device may accommodate with the practice of this invention include, but not limited thereto, the following: ablation catheters, guidewires, pacing leads, pacing catheters, pacemakers, visualization and recording devices, drugs, and drug delivery devices, lumens, steering devices or systems, drug or cell delivery catheters, fiber endoscopes, suctioning devices, irrigation devices, electrode catheters, needles, optical fiber sensors, sources of illumination, vital signs sensors, and the like Theses devices may be deployed for procedures in an integral body part or space.

Although not shown, as mentioned above, the insertion of the electrode catheter into the epicardial region may be aided by the use of an access needle and subsequent passage of a guidewire. The access needle may first be inserted into the epicardium, with the guidewire then put in place. The electrode catheter may then be coaxially slid over the guidewire to access the epicardial region.

Although not shown and involving another approach, the insertion of a sheath into the epicardial region may be aided by the use of an access needle and subsequent passage of a guidewire. The access needle may first be inserted into the epicardium, with the guidewire then put in place. The sheath may then be coaxially slid over the guidewire to access the epicardial region. After positioning the sheath in the desired position, the catheter may then be inserted through the sheath to reach the epicardium.

For example, with present invention, an epicardial access needle-stick is may be implemented in the subxiphoid area of the chest and the catheter device must then only be advanced a short distance to get to the heart. However, it may immediately be steered through an acute angle to avoid the heart itself. Because of this, aspects of the present invention devices and those used in conventional techniques can be contrasted. For instance, conventional endocardial catheters may typically be 100 cm in length or longer since they must go from the leg to the heart, while an embodiment of the present invention electrode catheter could be, for example, about 30 cm or less since it may only need to go from the chest to the heart. It should be appreciated that the length may be greater than 30 cm as well. Similarly, catheters in excess of the required 30 cm could be an awkward physical obstacle that would interfere with the procedure and, if inadvertently bumped or moved, could injure the patient. Similarly the conventional long catheters used in cathode and ablation devices, while not dangerous as such, are nevertheless awkward. Another reason that present invention shorter catheters may be preferred in epicardial procedures is that it is easier to effect rotation of the distal end of a catheter through rotation of the proximal end if the length of the catheter is shorter. Therefore, a shorter sheath and catheter would be less awkward, easier to use, and safer.

It should be appreciated that various embodiments of the present invention electrode catheter may have a total length of less than about 200 cm, less than about 100, less than about 50 cm, less than about 25 cm, or less than about 20 cm, or may be shorter even yet if desired or required. It should be appreciated that the total length may be longer than any of the ranges provided above.

Although not shown, in another exemplary embodiment the electrode catheter 6 may be placed endocardially in order to receive transmitted energy from an epicardial ablation catheter or another endocardial ablation catheter.

FIG. 6 schematically illustrates a cross sectional view of an exemplary embodiment of the electrode catheter located on the proximal portion. The fluid lumen 22 and second fluid lumen 23 occupy internal cross-sectional area of the electrode catheter 6. The fluid lumen 22 may extend from the proximal fluid aperture 7 (for example, as shown in FIG. 1) to the distal fluid aperture 2 (as shown in FIG. 3). The second fluid lumen 23 may extend from the second proximal fluid aperture 13 (as shown in FIG. 1) to the second distal fluid aperture 30 (as shown in FIG. 3). The steering pull-wire or tensioning means 24 for controlling the steering means and second steering means are also shown. The steering tensioning means 24 extend from the control handle 8 (for example, as shown in FIG. 1) through the body catheter 6 and terminate at or near a point of curvature (for example, as referenced as A and B of FIG. 2). In this particular embodiment, there are two distal steering means (bi-directional control) and one proximal steering means (uni-directional control). Many other configurations of the steering tensioning means for adjustable positioning and digitation can be implemented. The stabilization pull-wire or tensioning means 25 for the deployment of the stabilization means are also shown. The stabilization tensioning means 25 extend from the control handle 8 (for example, as shown in FIG. 1) through the body of the catheter 6 and terminate at or near the stabilization means 25 at the distal portion 45 of the electrode catheter 6. Lastly, the electrical lead wire(s) 26 for the electrode is shown. The lead wire 26 may extend from the control handle 8 through the body of the catheter 6 and terminates at the electrode 3 at the distal portion 45 of the electrode catheter 6.

Figure 7:
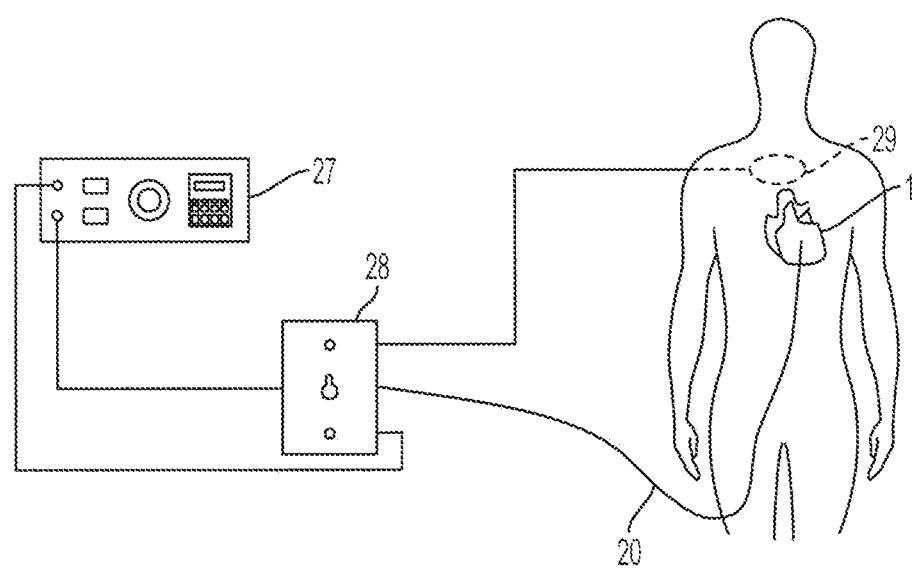
FIG. 7 schematically illustrates a diagram representing the standard existing approach to endocardial ablation therapy, wherein an electrode is placed on or in the exterior proximity of a patient's back.

FIG. 7 schematically illustrates an approach to endocardial ablation therapy, in contrast to the method of the subject invention. The figure may follow most of the details of FIG. 1 from J. C. Lin, "Catheter Microwave Ablation Therapy for Cardiac Arrhythmias," Bioelectromagnetics, Vol. 20, pp. 120-132, (1999), incorporated by reference herein in its entirety. In an approach, an endocardial catheter, 2, is placed in the heart of a patient as is known in the art. A radio frequency generator 27 is used to produce a high frequency or radio frequency AC signal that is passed to the tip of the endocardial ablation catheter 20 when the system switch 28 is closed by the operator. A return path for the RF energy is provided by the dispersive electrode 29 (as shown with dashed lines) that is mounted on the back of the patient in proximity to the heart. This approach stands in contrast to that of the subject invention, as illustrated in detail in FIGS. 1-6, and discussed throughout.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

One skilled in the art can see that many other embodiments of means and methods for using the electrode catheter in the ablation of cardiac tissues according to the technique of the invention, and other details of construction and use thereof, constitute non-inventive variations of the novel and insightful conceptual means, system and technique which underlie the present invention.

EXAMPLES

Practice of the invention will be still more fully understood from the following examples, which are presented herein for illustration only and should not be construed as limiting the invention in any way.

Example No. 1

In a specific example embodiment, the overall length of the electrode catheter from the distal end to the proximal end is approximately 30 cm: 5 cm from the distal tip of the catheter to the distal steering point, 15 cm from the distal steering point to the proximal steering point, and 10 cm from the proximal steering point to the control handle or proximal fluid aperture. The electrode catheter is nominally 8 french in about 2.7 mm. The catheter further comprises a platinum cathode at the distal tip having a semi-cylindrical geometry (an arc of 180 degrees), a circumference of 5.7 mm (consistent with the 8 Fr size), and an axial length of 25 mm. Additionally, the catheter comprises two distal fluid apertures of different sizes, wherein the larger of the two apertures is used for suction of fluid and the smaller is used for emission of fluid, preventing tamponade. Further, the catheter is steerable at two points along its axial length. Finally, the catheter is able to deploy two side flaps or extensions that, when open, work to rotationally stabilize the catheter so that it can not flip over, thus providing confidence that only the desired side of the device would be facing the heart during heating or usage.

REFERENCES CITED

The following patents, applications and publications as listed below and throughout this document are hereby incorporated by reference in their entirety herein.

The devices, systems, compositions and methods of various embodiments of the invention disclosed herein may utilize aspects disclosed in the following references, applications, publications and patents and which are hereby incorporated by reference herein in their entirety:

U.S. PATENT AND APPLICATION DOCUMENTS

| U.S. Pat. AND APPLICATION DOCUMENTS | | | |
|---|---|---|---|
| 7,147,633 | December 2006 | Chee et al | 606/41 |
| 7,146,225 | December 2006 | Guenst et al | 607/119 |
| 7,101,362 | September 2006 | Vanney | 604/523 |
| 7,090,637 | August 2006 | Danitz et al | 600/141 |
| 7,041,099 | May 2006 | Thomas et al | 606/41 |
| 6,974,454 | December 2005 | Hooven | 606/41 |
| 6,960,205 | November 2005 | Jahns et al | 606/41 |
| 6,916,318 | July 2005 | Francischelli et al | 606/41 |
| 6,849,075 | February 2005 | Bertolero et al | 606/41 |
| 6,827,715 | December 2004 | Francischelli et al | 606/34 |
| 6,827,714 | December 2004 | Swanson | 606/32 |
| 6,752,805 | June 2004 | Maguire et al | 606/41 |
| 6,723,092 | April 2004 | Brown et al | 606/41 |
| 6,689,128 | February 2004 | Sliwa et al | 606/41 |
| 6,558,382 | May 2003 | Jahns et al | 606/41 |
| 6,231,518 | May 2001 | Grabek et al | 600/508 |
| 6,206,004 | May 2001 | Schmidt et al | 604/500 |
| 6,156,009 | December 2000 | Grabek | 604/117; |
| 5,972,013 | October 1999 | Schmidt | 606/185 |

U.S. Pat. Application Publication 2002/0045895 A1 to Sliwa et al., Apr. 18, 2002

FOREIGN PATENT DOCUMENTS

| FOREIGN PATENT DOCUMENTS | | |
|---|---|---|
| EP | 1181896 | February 2002 |
| WO | 01/05306 | January 2002 |
| WO | 01/80757 | November 2001 |
| WO | 01/68173 | September 2001 |
| WO | 01/58373 | August 2001 |

-continued

| FOREIGN PATENT DOCUMENTS | | |
|---|---|---|
| WO | 01/80724 | April 2001 |
| WO | 99/18869 | April 1999 |
| Au | 70522/96 | October 1996 |
| WO | 95/10319 | April 1995 |
| DE | 43 13 903 | September 1994 |
| WO | 93/20886 | October 1993 |
| EP | 0 450 608 | October 1991 |
| CA | 2236958 | July 1973 |

OTHER PUBLICATIONS

A. d'Avila et al., "Transthoracic Epicardial Catheter Ablation of Ventricular Tachycardia," Heart Rhythm, Vol. 3, pp. 1110-1111, (2006).

E. Sosa et al., "Epicardial Mapping and Ablation Techniques to Control Ventricular Tachycardia," Journal of Cardiovascular Electrophysiology, Vol. 16, pp. 449-452, (2005).

S. Mahapatra et al., "Incidence and Predictors of Cardiac Perforation after permanent Pacemaker Placement," Heart Rhythm, Vol. 2, pp. 907-911, (2005).

D. L. Packer et al., "Multimodality 3-D Ultrasound and Computed Tomographic Image Fusion: A Novel Basis for Catheter Navigation and Electroanatomic Mapping," Circulation, Vol. 112, p. U684, (2005).

E. Sosa et al., "Nonsurgical Transthoracic Epicardial Approach in Patients with Ventricular Tachycardia and Previous Cardiac Surgery," Journal of Interventional Cardiac Electrophysiology, Vol. 10, pp. 281-288, (2004).

W. P. Beukema et al., "Radiofrequency Ablation of Atrial Fibrillation in Patients Undergoing Concommitant Cardiac Surgery. First Experience," PACE, Vol. 20 (Part II), p. 1100, (Apr. 1997).

L. S. Klein et al., "Radiofrequency Ablation of Cardiac Arrhythmias," Scientific American Science & Medicine, pp. 48-57, (May/Jun. 1994).

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced herein.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. An ablation catheter system, comprising:
   an energy source;
   an epicardial ablation catheter electrically connected to said energy source and configured to be disposed outside of a subject's heart in the middle mediastinum thorax of the subject, and to transmit ablating energy received from said energy source for ablating a portion of the subject's heart;
   an electrode catheter configured to be disposed in the intra-cardiac space of the subject and configured for use with said epicardial ablation catheter, said electrode catheter comprising:
      a proximal portion, a distal portion, and a longitudinal structure there between, and
      an electrode configured to receive the transmitted ablating energy from the epicardial ablation catheter when the epicardial ablation catheter is disposed outside of the subject's heart in the middle mediastinum thorax of the subject, wherein the electrode comprises a contoured structure having a semi-cylindrical shape with a longitudinal length parallel to the distal portion; and
      a stabilizing mechanism including at least one deployable member configured to transition between a retracted position and a deployed position by rotating or extending at least partially from inside an interior portion of the distal portion of the electrode and through a side of said distal portion of the electrode catheter while disposed in the body of the subject, wherein the stabilizing mechanism allows a rotational orientation of the electrode catheter to remain fixed in place relative to a surface of the heart so as to maintain a position of the contoured structure of the electrode proximate to the surface of the heart.

2. The system of claim 1, wherein said electrode catheter is configured to be disposed in the left ventricle.

3. The system of claim 1, wherein said electrode catheter is configured to be disposed in the right ventricle.

4. The system of claim 1, further comprising a steering mechanism configured to navigate said electrode catheter into position in the intra-cardiac space.

5. The system of claim 4, wherein said steering mechanism comprises at least one of the following: guide wire, pull string, tensioning line, or digitating distal tip.

6. The system of claim 1 further comprising an electrical lead in communication with said electrode for supplying other energy to said electrode.

7. The system of claim 1 wherein said electrode is contoured for receiving said transmitted ablating energy from said epicardial ablation catheter.

8. The system of claim 1, wherein said electrode catheter is configured to be used in conjunction with said epicardial ablation catheter for the purpose of achieving localized thermal lesioning of heart tissues.

9. The system of claim 1, wherein said electrode catheter comprises a least one distal fluid aperture adapted for passage of a fluid.

10. A method of using an epicardial ablation catheter, which transmits ablating energy for ablating a portion of a heart, and an electrode catheter including an electrode, the electrode comprising a contoured structure having a semi-cylindrical shape with a longitudinal length parallel to a distal portion of the electrode catheter, said method comprising:
   disposing at least the distal portion of the electrode catheter in the intra-cardiac space of a subject;
   stabilizing the electrode catheter in the intra-cardiac space of the subject via a stabilizing mechanism, said stabilizing including rotating or extending the stabilizing mechanism at least partially from inside an interior portion of the distal portion of the electrode and through a side of the distal portion of the electrode catheter, wherein the stabilizing mechanism allows a rotational orientation of the electrode catheter to remain fixed in place relative to a surface of the heart so as to maintain a position of the contoured structure of the electrode proximate to the surface of the heart;
   disposing the epicardial ablation catheter outside of the heart in the middle mediastinum thorax of the subject; and
   receiving the transmitted ablating energy from the epicardial ablation catheter with the electrode catheter.

11. The method of claim 10, wherein the intra-cardiac space includes the left ventricle.

12. The method of claim 10, wherein the intra-cardiac space includes the right ventricle.

13. The method of claim 10, further comprising:
   navigating the distal portion of the electrode catheter into a desired position in the intra-cardiac space using a steering mechanism of the electrode catheter.

14. The method of claim 10, wherein the electrode catheter is used in conjunction with the epicardial ablation catheter to provide localized thermal lesioning of heart tissues.

15. The method of claim 10, wherein said electrode catheter comprises a least one distal fluid aperture adapted for passage of a fluid.

16. An ablation catheter system, comprising:

an energy source;

an epicardial ablation catheter electrically connected to said energy source and configured to be disposed outside of a subject's heart in the middle mediastinum thorax of the subject, and to transmit ablating energy received from said energy source for ablating a portion of the subject's heart;

an electrode catheter configured to be disposed in the intra-cardiac space of the subject and configured for use with said epicardial ablation catheter, said electrode catheter comprising:

a proximal portion, a distal portion, and a longitudinal structure there between, and an electrode configured to receive the transmitted ablating energy from the epicardial ablation catheter when the epicardial ablation catheter is disposed outside of the subject's heart in the middle mediastinum thorax of the subject, wherein the electrode comprises a contoured structure having a semi-cylindrical shape with a longitudinal length parallel to the distal portion; and a stabilizer configured to stabilize said distal portion of the electrode catheter while disposed in the intra-cardiac space of the subject, the stabilizer comprising at least one deployable member configured to transition between a retracted position and a deployed position by rotating or extending at least partially through a slot in a side of said distal portion of the electrode catheter, wherein the stabilizer allows a rotational orientation of the electrode catheter to remain fixed in place relative to a surface of the heart so as to maintain a position of the contoured structure of the electrode proximate to the surface of the heart.

17. The system of claim 16, wherein said electrode catheter comprises a least one distal fluid aperture adapted for passage of a fluid.

\* \* \* \* \*